United States Patent [19]

Preikschat et al.

[11] Patent Number: 5,834,635
[45] Date of Patent: Nov. 10, 1998

[54] PLUG FLOW CONVERTING PIPELINE AND METHOD

[76] Inventors: Ekhard Preikschat, P.O. Box 981, Bellevue, Wash. 98009-0981; Michael G. Stern, 106-219th St., Bothell, Wash. 98021

[21] Appl. No.: 846,120

[22] Filed: Apr. 25, 1997

[51] Int. Cl.⁶ .............................. G10N 11/00; F25C 1/00; C07C 1/00
[52] U.S. Cl. ...................... 73/53.01; 73/64.41; 73/61.41; 73/53.04
[58] Field of Search .............................. 73/53.01, 53.03, 73/54.04, 61.41, 61.71, 64.41, 61.43

[56] References Cited

U.S. PATENT DOCUMENTS

| | | | |
|---|---|---|---|
| 2,973,000 | 2/1961 | Pearson | 137/91 |
| 4,095,457 | 6/1978 | Koda et al. | 73/53 |
| 4,253,329 | 3/1981 | Karnis | 73/63 |
| 4,267,699 | 5/1981 | Bahrenburg | 62/66 |
| 4,492,116 | 1/1985 | Gillier et al. | 73/432 R |
| 4,677,846 | 7/1987 | Lundberg | 73/63 |
| 4,754,639 | 7/1988 | Rich et al. | 73/53 |
| 4,803,869 | 2/1989 | Barcelona et al. | 73/53 |
| 4,888,981 | 12/1989 | Johansen et al. | 73/60.1 |
| 5,258,563 | 11/1993 | Gosling et al. | 585/322 |
| 5,325,709 | 7/1994 | Lee | 73/61.43 |
| 5,600,058 | 2/1997 | Preikschat et al. | 73/54.32 |

*Primary Examiner*—Hezron E. Williams
*Assistant Examiner*—J. David Wiggins
*Attorney, Agent, or Firm*—Dean A. Craine

[57] ABSTRACT

A plug flow converting pipeline and method for creating a plug flow condition of a fluid in a pipeline or similar conduit so that a desired measurement of the fluid may be conducted. In one embodiment, the converting pipeline includes a section of pipeline with an elongated flow channel disposed therein. The flow channel acts to reduce the amount of energy stored in the fluid fibers thereby enabling them to re-flocculate and form a plug flow condition. While a sufficient length of straight pipeline may enable the fibers to re-flocculate, the flow channel provides a "calming effect" thereby enabling the overall length of straight pipeline to be reduced. In another embodiment, the pipeline includes a T-shaped transition piece attached to the pipeline designed to create a chaotic flow condition which quickly transforms into a plug flow condition, thereby requiring a shorter length of straight pipeline.

7 Claims, 2 Drawing Sheets

PLUG FLOW CONVERTING PIPELINE AND METHOD

BACKGROUND OF THE INVENTION

1. Field of the Invention

The present invention is directed to pipelines and, more specifically, to pipelines and methods used to carry fluids in a plug flow state for accurate measurement of the consistency, viscosity or rheological properties of a fluid.

2. Description of the Related Art

The processing of a pulp stream depends directly on the consistency of the moving pulp slurry, where consistency is defined as the weight of the dried fiber as a percentage of total weight of fiber and water. To date, the most widely used method for measuring the consistency is based on a mechanical measurement of the shear forces exerted by a moving pulp slurry on a sensing element, for example, as described in U.S. Pat. No. 5,600,058 and applicant's pending U.S. patent application, Ser. No. 08/666,903.

This type of in-line, mechanical measurement of shear force has long been used to determine particular properties of the fluid flow, which are necessary to control a chemo-mechanical process. A fluid flow has very complex flow dynamics. A two phase fluid system, as encountered in a pulp stream, is even more complex and the resulting hydrodynamics of the flow pattern are not always known or predictable. Yet, in order to achieve a good shear force measurement, it is important that the fluid flow behaves uniformly over the entire measuring region.

In the paper industry, the measurement of the consistency of the pulp slurry is of particular interest at the headbox of a paper machine. At the "wet-end" of a paper machine, consistency of the-pulp slurry translates directly into how much pulp fiber is deposited "on the wire" (of a paper machine) and the resulting thickness (or basis weight) of the dried sheet of paper. Headbox consistencies are typically in the range from 0.5 to 1.0%. This is much lower than the consistencies encountered further upstream, like those at the machine chest, which are typically around 2 to 4%.

In a straight section of pipeline, the pulp, at consistencies above 2%, moves as a solid plug, with all of its elements moving at the same velocity-with no relative motion between neighboring elements. In the pulp and paper industry, this type of flow is referred-to as a "plug flow" condition. The consistency transmitter described in U.S. Pat. No. 5,600,058, works best when the sensing element is disposed in the pulp stream moving under plug flow conditions.

Plug flow conditions are entirely different from classical flows involving single phase fluids. The latter is characterized as being-laminar or turbulent depending on the Reynold's number which is based on classical Newtonian fluid mechanics. Under plug flow conditions, the individual pulp fibers no longer move-as independent fluid elements, but instead they are held in place by an interlocking fiber network. The fiber network is formed under specific conditions which depend on (i) the pulp consistency, (ii) fiber length, (iii) the flow speed of the pulp stream, and (iv) the length of straight pipe section located immediately ahead of the measuring point. In particular, it depends on the time the pulp takes to move from an energy source (A), like a pump or a flow perturbing turn in the pipeline, to the measuring point (B). If the transit time between (A) and (B) is long enough to allow the pulp fibers to dissipate all stored energy caused by a disruptive force, then the pulp fibers lock-back into place to reestablish the fiber network. When this occurs, the pulp flow is said to have "re-flocculated."

An instrument like the one described in U.S. Pat. No. 5,600,058, measures the force required to break up the fiber network of a flocculated fiber stream, known as the "yield stress" of the fiber network. However, if the fiber stream has not, "re-flocculated" to form a plug flow, the measurement of the "yield stress" will be inaccurate. For example, in an actual pulp stream of softwood fibers at 1.6% consistency, an instrument may be located downstream 54 inches from an elbow of an 18 inch ID pipeline. At this location, the instrument will indicate a consistency of 0%, which is the same reading obtained when measuring in air under no torque conditions. Such an indication suggests that the sensing element is located in an air pocket, even though the pipeline is pressurized to 45 psi (about three times atmospheric pressure). When the pump, located five pipeline diameters upstream from the instrument is shut down, the torque measurement returns to its expected reading of 1.6% consistency. If the instrument is then relocated a distance of six pipeline diameters, approximately 108 inches, downstream from the elbow, the instrument produces a reading of 1.1%, about 69% of the expected reading. By extrapolation, these results indicate that the instrument should be located approximately ten pipeline diameters downstream from the elbow.

It should also be recognized that at lower pulp consistencies, or using shorter fibers, or at higher flow speeds, the distance between the elbow and the instrument should be even longer to re-establish plug flow conditions. In a cramped mill it is not always possible to find such long, straight sections of pipeline, and hence another solution to this problem must be found.

The invention disclosed herein addresses this problem. Even though this invention makes specific reference to pipelines and methods for accurate measurements of a pulp slurry, it should be understood that the invention can be used on other types of pipelines or conduits designed to carry other types of fluids, e.g. natural and synthetic fibers like cotton, wool and kevlar fibers, as well as many other kinds of fluids, e.g. molasses in the crystallization process leading to the production of refined sugar.

SUMMARY OF THE INVENTION

It is a general object of the present invention to provide a pipeline having means for modifying an unregulated fluid flowing within the pipeline to produce a uniform and predictable flow over a specific region of the pipeline for measuring a desired parameter, e.g. consistency.

It is another object of the invention to provide such a pipeline which allows a measuring device to be used over a wide range of flow, consistency and pipeline diameters without degrading the measurement.

Disclosed herein is a pipeline which includes means for creating a plug flow condition for the fluid flowing therein so that the consistency of the fluid mat be determined by a rotating consistency transmitter, as shown in FIG. 1, or some other parameter measuring device whose accuracy is dependent, at least in part, upon the creation of a plug flow condition. In one embodiment, the pipeline includes an elongated flow channel longitudinally aligned and disposed inside the pipeline to produce a temporary plug flow condition. The flow channel is located directly over a rotating consistency transmitter's sensing element. More specifically, the flow channel has inlet and outlet openings which allow the fluid flowing inside the pipeline to enter and exit the flow channel. The width "W" of the flow channel is sufficiently large so that it does not interfere with the operation of the sensing element and does not obstruct the flow of fluid in the pipeline. The length "H" of the flow channel is determined by the required calming length "L" needed for pulp flowing in a pipeline to re-flocculate to form a plug flow condition. Generally, the calming length "L" is determined by the following: L=(4.25×V×D)/C×k) where "V" is the velocity of the pulp flow in feet per second, "D" is the diameter of the pipeline (in feet), "C" is the consistency of the pulp in %, and "k" is a dimension-less constant which depends on fiber length (1.0 for long fibers, 0.8 for TMP fibers, and 0.7 for short groundwood fibers).

When the pipeline has a straight run of length "P" which is less than the required calming length "L", then the flow channel is used to provide additional flow calming effect. The length of the flow channel "H" is then calculated by the equation:

$$H=[(4.25\times V\times D)/C\times k)-P]\times W/D$$

Typically, the flow channel is positioned over the sensing element so that approximately 80% of the overall length "H" of the flow channel is positioned upstream from the desired measuring region. During use, fluid under a turbulent condition flows into the flow channel and is then modified into a plug flow-condition. The measurement device then measures this fluid under the plug flow condition.

In another embodiment, the means for converting the fluid flow includes a T-shaped transition piece inserted along the, pipeline. Usually, the T-shaped transition piece creates a temporary chaotic flow condition. When the flow emerges from the T-shaped transition piece, it has less stored energy and the plug flow condition is more quickly established which thereby reduces the need for a calming length of pipeline.

Using the above means, a method of creating a plug flow condition in a pipeline is provided.

DESCRIPTION OF THE PREFERRED EMBODIMENT(S)

Figure 1:
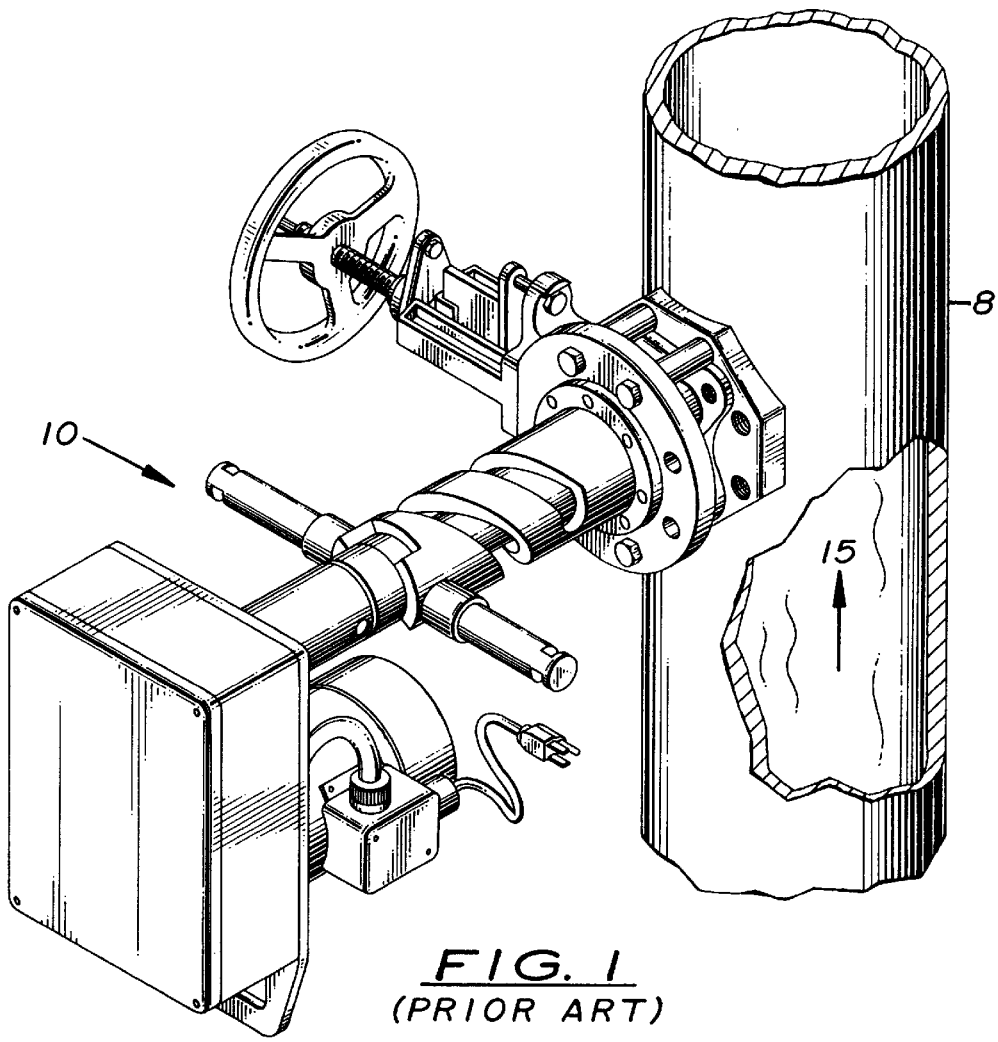
FIG. 1 is a perspective view of the prior art consistency transmitter installed through a gate valve directly connected to a pipeline carrying a pulp stream.

In this application, the apparatus 16 and method are described in an environment where the user wants to measure and control the consistency of a pulp stream 15 flowing through a pipeline 8 to the headbox of a paper machine (not shown). This typically involves a pipeline 8 with a large diameter, the pulp stream 15 flowing through the pipeline 8 at a high speed, and the pulp stream 15 having a consistency below 1%. The present invention shown used with a consistency transmitter 10, as shown in FIG. 1, described in U.S. Pat. No. 5,600,058, and incorporated herein. The consistency transmitter 10, which is installed in the pipeline 8 upstream from the headbox of the paper machine, includes a rotating sensing element 14 which is positioned directly in the pulp stream 15 as shown more clearly in FIGS. 3 and 4.

Under conditions described above, the pulp stream 15 is not likely to be flowing under plug flow conditions, but rather will follow a spiraling path within the pipeline 8. The concept of a "calming length" in a pipeline was introduced some 20 odd years ago by Eur-Control, a Swedish company, in connection with the application of an optical pulp flow meter, which uses an optical correlation principle and required plug flow conditions for proper measurement of flow. The "calming length" is the length of straight segment of pipeline pipe run that is necessary for plug flow conditions to be re-established. At that time Eur-Control published an application guide (No. D218.80/2a) which gave the following empirically derived equation for the calming length L:

$$L=(4.25\times V\times D)/C\times k),$$

where "V" is the velocity of the pulp flow in feet per second, "D" is the diameter of the pipeline, (in feet), "C" is the consistency in %, and "k" is a dimension less constant which depends on fiber length and is 1.0 for long softwood fibers 0.8 for TMP fibers, and 0.7 for short ground wood fibers.

Figure 2:
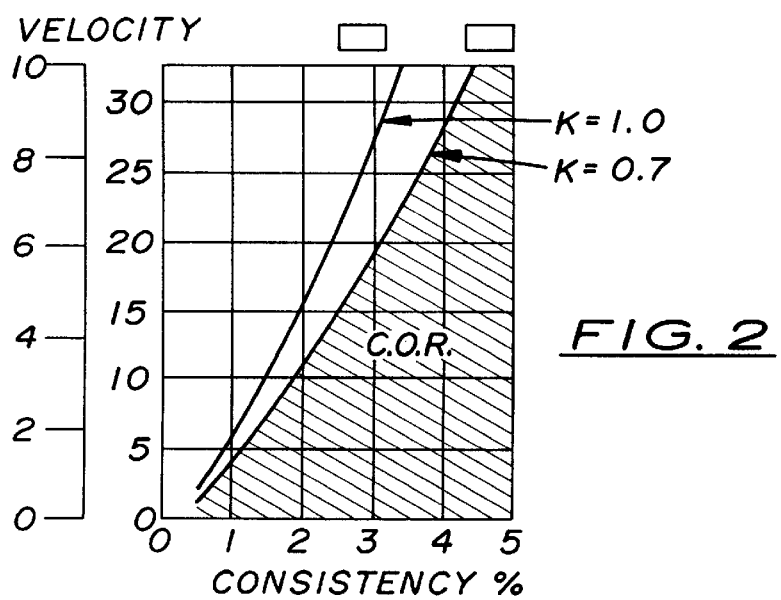
FIG. 2 shows the particular values of flow speed and consistency of a pulp stream that are required so as to obtain plug flow conditions.

FIG. 2 shows the relationship between flow velocity (shown as the ordinate—in m/sec as well as fps), the pulp consistency (C)(shown as the abscissa in %), and two values of k. The areas below the respective curves is the region where the calming length is long enough to realize plug flow conditions.

Taking the above described case at the headbox of a paper machine, with a pulp consistency (C) of 1%, an 18 inch diameter (D) pipeline, a flow velocity (V) of 6 fps, and k=1.0, the calming length is 38.25 feet. In most instances, it would be very hard to find a straight segment of pipeline with this sufficient length.

However, considering that the rotating sensing element 14 has an outside diameter of only 2.8 inches, the sensing element 14 only measures a very small fraction of the cross-section of the pipeline 8. This means one can artificially create a small flow zone within the larger pipeline 8, which meets the above, calming length criteria.

Figure 3:
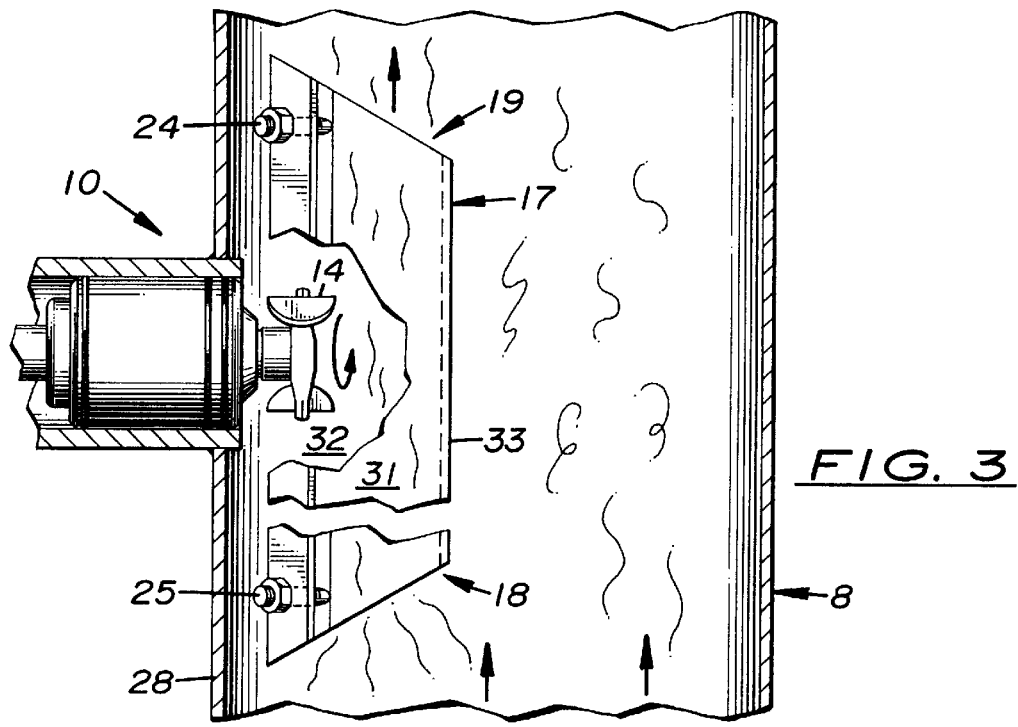
FIG. 3 is a larger side view of the pipeline with an energy dissipating flow channel positioned in front of the measuring region.
Figure 4:
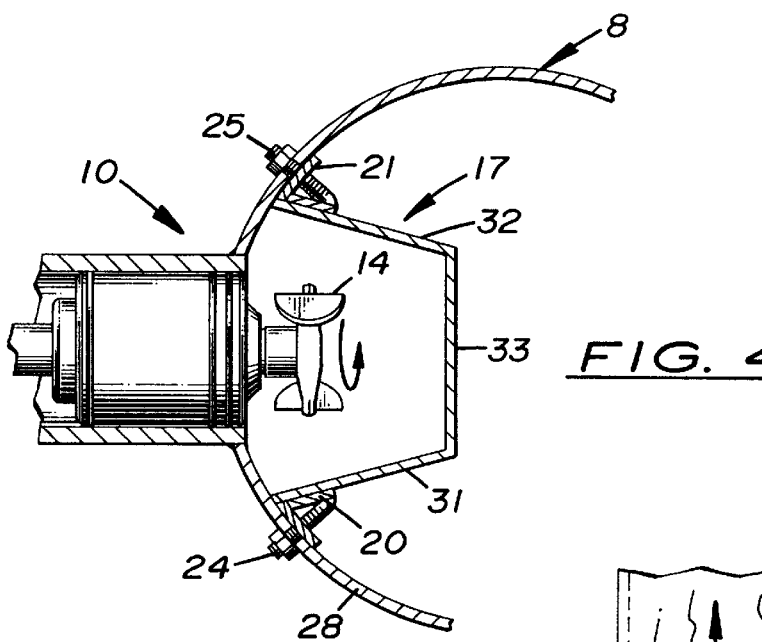
FIG. 4 is a front view of the energy dissipating flow channel.

FIGS. 3 and 4 show a flow channel 17 designed to create a small flow zone inside the pipeline 8. In the embodiment show, the flow channel 17 is approximately 4 inches square in cross section and 40 inches in length. The flow channel 17, which is mounted in the pipeliner 8 over the sensing element 14, has an inlet opening 18 and an outlet opening 19 which enables a portion of the pulp stream 8 to flow through the flow channel 17 during use. In the embodiment shown, the flow channel 17 is square in cross section and produces a higher energy dissipation as compared to being circular in cross-section. The flow channel 17 is made of rigid material, such as stainless steel or aluminum, and has two side walls 31, 32 and one top plate 33. Brackets 20 and 21 are fitted on both side walls 31, 32, respectively, to reinforce the flow channel 17 and prevent any distortion therein. These brackets 20, 21 are also used to attach the flow channel 17 to the inside surface of the pipeline 8, via two pairs of mounting bolts 24, 25, which extend transversely through the wall of the pipeline 8.

During assembly, the flow channel 17 is positioned longitudinally inside the pipeline 8. The length "H" of the flow channel 17 is determined by the required calming length "L" needed for the pulp to re-flocculate and form a plug flow condition in the pipeline 8. If the pipeline 8 has a straight section of length "P", which is less than the required calming length "L" as calculated to the above equation, then the flow channel 17 must be used to provide additional flow calming effect. The length "H" of the flow channel 17 is then calculated by the following equation:

$$H = (L-P) \times (W/D)$$

where "W" is the width of the flow channel 17 and "D" is the diameter of the pipeline 8. It should be noted that the length "H" is based on a circular pipeline 8, in practice, however, a square, cross sectional shaped flow channel 17 will be more effective in producing the desired calming effect than a circular, cross sectional shaped flow channel 17, i.e. the length given by the above formula is a worst case scenario. When the length "P" of the pipeline 8 is almost long enough to provide the required calming effect, it may suffice to modify the flow channel 17 to include only one or both sidewalls 31, 32 and eliminate the top plate 33.

Typically, the flow channel 17 is positioned over the sensing element 14 with the inlet opening 18 positioned a distance approximately 80% of the height (H) upstream from the sensing element 14. The outlet opening 19 is then positioned approximately 20% (H) downstream from the sensing element 14.

The flow channel 17 may be mounted in an existing pipeline 8 by cutting out a section of the pipeline 8 and then welding flanges to the ends of the pipeline 8 and to the cut out section, to connect the cut out section to the main pipeline 8. Alternatively, for a large diameter pipeline, it may actually be more economical to cut a large opening into the pipeline 8 opposite to the region of measurement. The flow channel 17 can then be inserted through this opening and installed in place over the desired location inside the pipeline 8. This opening can be fitted with a flange and a removable cover plate, which can be removed at a later time for service and/or inspection.

It should be noted that the spiraling flow action created directly behind a bend in a large pipeline 8 is, in large part, caused by the Coriolis force. When the individual parts of a flow are forced to deviate from their smooth, straight line, inertial path to follow the curve of a bend, they are forced into a spiraling flow pattern. However, if the flow originates from a chaotic flow zone, then the effect of the Coriolis force is diminished. It is believed that the flow pattern of the individual parts exiting the chaotic zone are largely random. The energy stored by these randomly moving flow parts is more quickly dissipated as compared to the energy when the parts are coherently traversing on a spiraling path.

Figure 5:
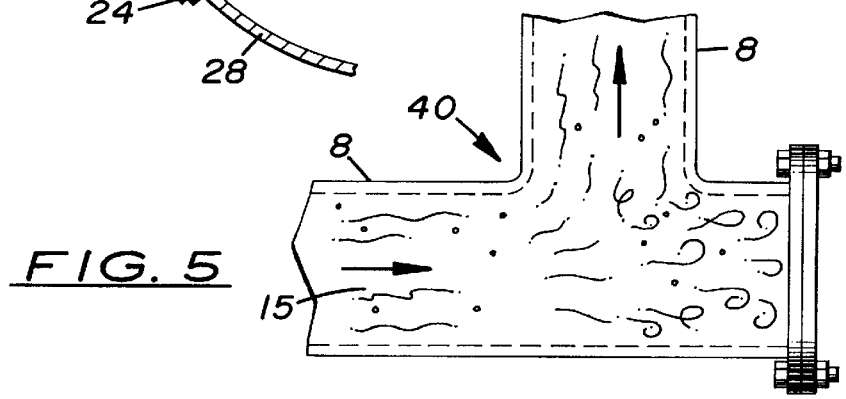
FIG. 5 shows a T-shaped transition piece which creates a chaotic flow action to break up the spiraling flow action in a pipeline thereby creating a plug flow condition.

FIG. 5 shows one simple way to achieve a chaotic flow zone by using a T shaped transition piece 40 instead of a smooth elbow in the pipeline 8. The flow inside the T shaped transition piece 40 is completely random but once the individual flow parts are moving downstream from the transfer section, the flow very quickly becomes coherent again, on a much faster scale than that given by the formula above for the calming length. A T-shaped transition piece 40 may be just as effective in removing spiraling flow action as compared to installing a square channel. In many cases, however, the latter solution may be cheaper when fitted retroactively.

In compliance with the statute, the invention, described herein, has been described in language more or less specific as to structural features. It should be understood, however, the invention is not limited to the specific features shown, since the means and construction shown comprised only the preferred embodiments for putting the invention into effect. The invention is, therefore, claimed in any of its forms or modifications within the legitimate and valid scope of the amended claims, appropriately interpreted in accordance with the doctrine of equivalents.

I claim:

1. A flow converting pipeline, comprising:
   a. pipeline capable of transporting a fluid;
   b. an elongated flow channel longitudinally aligned and attached inside said pipeline, said flow channel having opposite inlet and outlet openings and sufficient length and width to calm flow turbulences of the fluid flowing inside said flow channel and create a plug flow condition.

2. A flow converting pipeline, as recited in claim 1, wherein said flow channel having a length (H) and width (W) in accordance with the following equation:

$$H = (L-P) \times (W/D),$$

where "D" is the diameter of the pipeline (in feet), "L" is the required calming length of the straight pipeline, and "P" is the actual length of straight pipeline.

3. An apparatus as recited in claim 1, wherein said flow channel is disposed in said pipeline so that said inlet opening is positioned a distance upstream from the desired effect approximated 80% of the overall length of the flow channel.

4. An apparatus as recited in claim 1, wherein said flow channel is square in cross-section.

5. A flow converting pipeline for alternating the flow of fluid therein so as to facilitate accurate measurement of consistency, viscosity, or rheological fluid properties, comprising:
   a. a pipeline capable of transporting a fluid; and,
   b. a T-shaped transition piece attached to said pipeline for converting the fluid flowing into a plug flow condition.

6. A method of creating a plug flow condition of a fluid flowing in a section of pipeline, comprising the following steps:
   a. selecting a means capable of being attached to a section of pipeline to partially or completely convert the fluid flowing therein into a plug flow condition, said means being an elongated flow channel disposed longitudinally inside the pipeline, said flow channel having a inlet opening and an outlet opening, said flow channel having a sufficient length and width to calm flow turbulences of the fluid flowing inside said flow channel; and
   b. transporting a fluid through said pipeline.

7. A method of creating a plug flow condition of a fluid flowing in a section of pipeline so as to facilitate accurate measurement of consistency, viscosity, or rheological properties, comprising the following steps:
   a. selecting a T-shaped transition piece capable of being attached to a section of pipeline, said T-shaped transition piece capable of partially or completely converting the fluid flowing therein to a plug flow condition;
   b. attaching said T-shaped transition piece to said pipeline; and,
   c. transporting a fluid through said pipeline.

* * * * *